US00PP27088P2

(12) United States Plant Patent
Avent

(10) Patent No.: US PP27,088 P2
(45) Date of Patent: Aug. 23, 2016

(54) ***BAPTISIA* PLANT NAMED 'BLUE TOWERS'**

(50) Latin Name: ***Baptisia* hybrid**
Varietal Denomination: Blue Towers

(71) Applicant: Tony Avent, Raleigh, NC (US)

(72) Inventor: Tony Avent, Raleigh, NC (US)

( * ) Notice: Subject to any disclaimer, the term of this patent is extended or adjusted under 35 U.S.C. 154(b) by 221 days.

(21) Appl. No.: 13/999,947

(22) Filed: Apr. 8, 2014

(51) Int. Cl.
*A01H 5/02* (2006.01)

(52) U.S. Cl.
USPC ..... Plt./263.1

(58) Field of Classification Search
USPC ..... Plt./263.1
CPC ..... A01H 5/02
See application file for complete search history.

(56) References Cited

PUBLICATIONS http://www.rarefindnursery.com/index.php/perennials/baptisia-wild-indigo/baptisia-indigo-spires-false-indigo-19290.html; 2013; 2 pages.*

* cited by examiner

*Primary Examiner* — Kent L Bell

(57) ABSTRACT

A new and distinct plant cultivar of hardy herbaceous false indigo named *Baptisia* 'Blue Towers' characterized by tall upright habit, no basal foliage, and many large, dark purple-blue flowers held well above the foliage in the spring, suitable for landscaping as a specimen or en masse.

1 Drawing Sheet

Botanical classification: *Baptisia* hybrid.
Cultivar designation: 'Blue Towers'.

BACKGROUND OF THE INVENTION

The present invention relates to a new and distinct cultivar of hybrid *Baptisia* plant, botanically known as *Baptisia* 'Blue Towers' and will be referred to hereafter by its cultivar name, 'Blue Towers'. The new cultivar represents a new false indigo, a hardy herbaceous perennial grown for landscape and cut flower use.

The new invention arose from an ongoing breeding program at a nursery in Raleigh, N.C.

*Baptisia* 'Blue Towers' was hybridized by Tony Avent in April of 2003 at a nursery in Raleigh, N.C. and originally given the breeder code of #2004-157. The female or seed parent was a proprietary selection of *Baptisia australis* (not patented) and the male or pollen parent was a proprietary selection of *Baptisia alba* (not patented). The instant plant was initially selected for further evaluation in spring 2005. The goals of the hybridizing program have been to develop *Baptisia* hybrids with improved garden-worthy characteristics and tall upright habit and flowers visible well above the foliage. 'Blue Towers' was selected as a single unique plant by the inventor in 2005 and first asexually propagated by stem cuttings in May 2008 at the same nursery in Raleigh, N.C. The novel characteristics of 'Blue Towers' have since been determined to be stable and reproduce true to type in successive generations of asexually propagated plants.

SUMMARY OF THE INVENTION

The novel traits of 'Blue Towers' have been repeatedly observed and represent the novel and improved characteristics of the new cultivar as observed for multiple generations over the past five years. The following characteristics in combination distinguish 'Blue Towers' from other varieties of *Baptisia* known to the inventor:

1. Exceptionally upright and tall plant habit;
2. No basal foliage;
3. Flower stalks held well above foliage for high visibility;
4. Large, dark purple-blue flowers.

The nearest comparison plant is the female parent, a proprietary selection of *Baptisia australis*. Compared to the female parent 'Blue Towers' is more erect and taller. Compared to the male parent, a proprietary selection of *Baptisia alba*, the new plant has larger, dark purple-blue flowers and the male parent has smaller near-white flowers.

BRIEF DESCRIPTION OF THE DRAWINGS

The photographs of the new plant demonstrate the unique traits of the new plant and the overall appearance. The colors are as accurate as reasonably possible with color reproductions. Variation in ambient light spectrum, source and direction may cause the appearance of minor variation in color. The accompanying photograph is of a three-year old plant growing in an open full-sun trial garden in Raleigh, N.C.

The drawing shows the habit of a plant in full flower.

DETAILED BOTANICAL DESCRIPTION OF THE PLANT

The following is a detailed description of 3 year-old plants of the new cultivar as grown outdoors in a trial plot at a wholesale nursery in Zeeland, Mich. Plants of the new cultivar have not been tested under all possible conditions. The phenotype may vary with changes in environment, climate, and cultural conditions without change however in the genotype. The color reference is in accordance with The 2001 edition of The Royal Horticultural Society Colour Chart except where general color dictionary terms are used.

Plant habit: Perennial, upright, branched, vase-shaped growth habit with long inflorescences held in and above the foliage.

Plant size: About 75 cm wide and 115 cm tall.

Roots: Fleshy, well-branched, deeply rooted.

Root color: Nearest RHS 161D.

Growth and propagation:

*Propagation method*.—Stem cuttings, rooting in about three weeks.

*Growth rate*.—Moderately, similar to other *Baptisia*.

Stems: Rigid and upright; glaucous; glabrous; cylindrical with longitudinal ridges and furrows; lower two nodes without leaves or branches; about 7 to 10 stems per plant; can produce 24 stems in six years; main stem up to 15 mm diameter at base and up to 115 cm tall to top of inflorescence, average about 95 cm tall and 12 mm diameter; normally about four alternately-arranged primary branches at 50 degree angle above horizontal, up to 36 cm long and 8 mm diameter, average for primary branches about 20 cm long and 6 mm diameter, smaller distally; and four alternately-arranged secondary branches per stem; four to five alternately-arranged tertiary branches up to 12.5 cm long and 3.0 mm diameter, average about 9 cm long and 2.5 mm diameter.

Stem color: Base between RHS 191B and RHS 191C with tinting of RHS N187B; apical stems tips nearest RHS 138A in shade and RHS N187B to top.

Stem scales: Acute apex and truncate base; dehiscing to leave behind thin scar; about 10 mm long and 10 mm wide at base.

Internodes: About 8.0 cm apart between lowest branches, average about 4.5 cm.

Foliage: Alternate on stem; ternate to palmately compound with three leaflets; outer two leaflets at about 60 degree angle to middle leaflet; up to 6.0 cm long and 9.0 cm wide, average 3.5 cm long and 4.5 cm wide.

Leaflet: Three, oblanceolate; apex obtuse to rounded, base attenuate; margins entire; petiolate; top surface matte, scaberulose below; size up to 6.0 cm long and 3.0 cm wide, average 3.5 cm long and 1.5 cm wide.

Venation: Pinnate, thin, not conspicuous, glabrous.

Vein color: Nearest RHS 137C above and below; main center vein nearest RHS 137C above and between RHS 138A and RHS 138B.

Leaflet color: Newly expanded closer to RHS 144A than to RHS N144C on upper and lower surfaces; mature upper and lower surface nearest RHS 137A.

Petioles: Glabrous; matte surface on top and below; about 1.5 cm long and 2.0 mm wide average 1.2 cm long and 2.0 mm wide; concaved facing upward.

Petiole color: Between 144A and 144B both surfaces.

Stipules: Lanceolate, acute apex with base truncate to stem; up to 2.5 cm long and 6 mm wide, average 1.0 cm long and 4.0 mm wide with largest stipules below primary branches and decreasing distally and on secondary branches.

Stipule color: Nearest RHS 138A both surfaces.

Flower: Zygomorphic, papilionaceous, non-secund, held at about 10 degree angle above horizontal; beginning about 50 cm above soil; about 125 flowers per main raceme and about 55 per secondary branch; seasonally effective for about 3 to 4 weeks beginning in early June in Zeeland, Mich. with about 40 flowers and 15 buds per stalk showing color during peak; individual flowers remain effective and on raceme for about three days; individually about 2.2 cm long, 1.5 cm tall and 1.3 cm wide at tallest and widest portions; an upper banner, a lower keel made up of two lobes folded around gynoecium and androecium; and two lateral wings or alae laterally appressed against keel.

Flower fragrance: None detected.

Peduncle: Rounded with ridges and furrows; glaucous; glabrous; from first flower to apex about 70 cm long; diameter at the base of first flower about 8.0 mm and about 2 mm diameter at the apex.

Peduncle color: Nearest RHS 144A in color with coating of nearest RHS 191A and tinted nearest RHS N187A in upper portions or where exposed to more light.

Pedicel: Round, glabrous, slightly glaucous; about 3.5 mm long and 1.0 mm diameter; color nearest RHS 138A with tinting of nearest RHS N187A.

Calyx: Campanulate, five-lobed with top lobe only dissected about 1.0 mm and other lobes dissected about 3.0 mm deep; apex obtuse, base fused in basal two thirds; margins entire; slightly glaucous; about 9.0 mm long and 5.0 mm diameter; persists after petal drop.

Calyx color: Base nearest RHS 138A, distal one-half developing tinting of nearest RHS N187A.

Buds one day prior to anthesis: Oblong reniform, flatted vertically; about 2.2 cm long and 9.0 mm tall and 5.0 mm wide.

Bud color: Keel petal lower center section nearest RHS N92A lightening to nearest RHS 93C toward edges with veining of between RHS N92D and RHS 93B; banner petal more red than RHS 93B and more blue than RHS N92D; gap between wings of banner petal nearest RHS 145D.

Petals: Five; with a lower fused keel, an upper banner, and two lateral wings or alae; keel comprised of two sections that are folded around stamens and pistil.

*Banner petal*.—Conduplicate, curved upward and backward and pinched in the middle; apex recuse, base claw-like; about 18 mm long and 9.0 mm wide; banner dorsal side color nearest RHS 94C at perimeter with the inner center portion nearest RHS N92D, ventral side perimeter nearest RHS 94D darkening to nearest RHS N92D with veining of between RHS 93C and RHS 93B in the lighter portions of both dorsal and ventral sides; claw portion nearest RHS 145C on both sides.

*Keel*.—Comprised of two main lobes that are folded around stamens and pistil; fused in the distal one-third with the apex notched or retuse and the bases separate and claw-like; top edge about one-third of the way from base has 3.0 mm smaller lobe pointing toward base; about 20 mm long and 9.0 mm tall with claw base narrowed to 2.0 mm wide for the basal 5.0 mm; color of outer RHS 90A keel side nearest RHS 90A near distal perimeter and lightening to RHS 145D on inside and outside, base claw nearest RHS 145D.

*Alae*.—Rounded apex and claw-like base; with 2.0 mm lobe pointing toward base and about one-third of the way from base; about 20 mm long and 8.0 mm tall with the claw narrowed to 2.0 mm wide for the proximal 5.0 mm; alae outside color nearest RHS 90A in distal portion and lightening to nearest RHS 91C before claw, inside color nearest RHS 90C distally and lightening to nearest RHS 91C before claw, claw nearest RHS 155C on both surfaces.

Receptacle: Disk-shaped, about 3.5 mm diameter and 1.5 mm depth; color nearest RHS 143A.

Gynoecium: One, with superior ovary.

*Pistil*.—About 17.0 mm long and 1.5 mm wide.

*Style*.—About 9.0 mm long and less than 1.0 mm diameter; color nearest RHS N144B.

*Stigma*.—Less than 0.5 mm diameter; color nearest RHS 145A.

*Ovary*.—Superior suspended by stipe; about 7 mm long and about 1.5 mm in diameter; color nearest RHS 144A.

*Stipe*.—About 3.0 mm long and 1.0 mm diameter; color nearest RHS 145B.

Androecium:

*Stamens*.—Ten, not united, 20.0 mm long; color nearest RHS 143A.

*Filament*.—1.9 cm in length and less than 1 mm in width; slightly curved upward at apex; filament color between RHS 145 B and RHS 145C; lighter at apex and base and darker in center.

*Anther*.—Dorsifixed, oblong; about 1.2 mm long and 0.6 mm wide; color nearest RHS 14B.

*Pollen*.—Spherical; abundant; color nearest RHS 17A.

Fruit: Slightly reniform; monocarpellate, dehiscing along two sides; oblong globose, about 4.0 cm long and 2.0 cm diameter with acute apical beak about 8.0 mm long and rounded base.

Seed: Reniform, compressed side to side, about 4.5 mm long, 2.0 mm thick and 3.0 mm tall; about 15 to 26 per fruit (open-pollinated); color between RHS 165A and RHS 165B.

Hardiness: To USDA zones 4 to 8; heavy clay or light loamy sand soils; able to withstand drought conditions once established.

Diseases: Susceptibility or resistance to diseases beyond that typically found in other false indigo plants has not been observed.

It is claimed:

1. A new and distinct cultivar of hardy herbaceous false indigo plant named *Baptisia* 'Blue Towers' as herein illustrated and described, with tall upright habit, and many large, dark purple-blue flowers held well above the foliage in the spring, suitable for landscaping as a specimen or en masse.

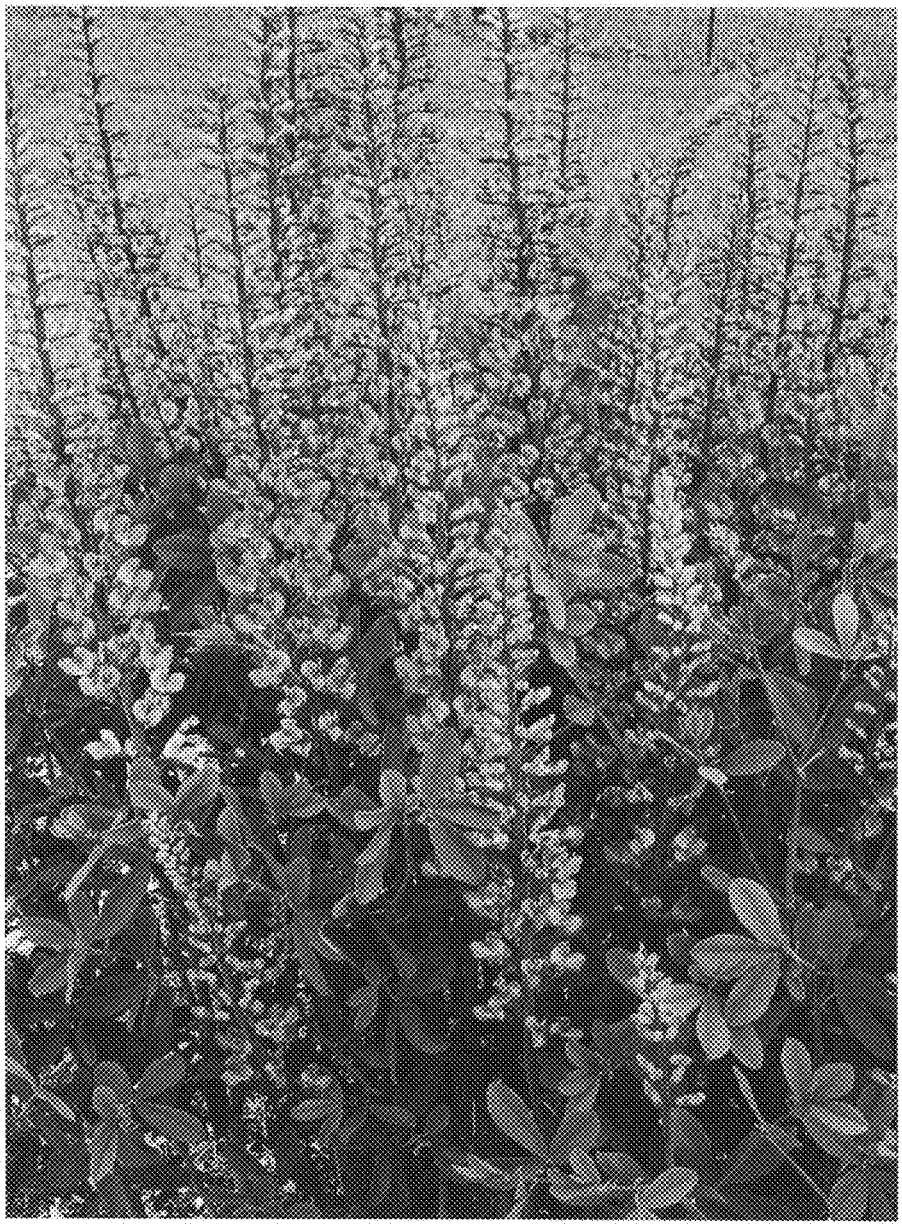

* * * * *